US00PP08561P

United States Patent [19]

Brizard

[11] Patent Number: Plant 8,561

[45] Date of Patent: Jan. 25, 1994

[54] SPRAY CARNATION NAMED MEDLEY

[75] Inventor: Jean Brizard, Paris, France

[73] Assignee: Laboratorie de Physiologie Vegetale, Le Pradet, France

[21] Appl. No.: 971,504

[22] Filed: Nov. 4, 1992

[51] Int. Cl.[5] ..... A01H 5/00
[52] U.S. Cl. ..... Plt./70.5
[58] Field of Search ..... Plt. 70.5

*Primary Examiner*—Howard J. Locker
*Assistant Examiner*—Elizabeth C. Kemmerer
*Attorney, Agent, or Firm*—Tilton, Fallon, Lungmus & Chestnut

[57] ABSTRACT

A new and distinctive spray carnation cultivar particularly distinguished by its medium size flowers having a pink color and round petals that are carried on an erect thick stem having more than 120 leaves.

1 Drawing Sheet

BACKGROUND OF THE NEW PLANT

This spray carnation cultivar originated as a hybrid seedling produced in my nursery at Le Pradet, France by my crossing of two plants, hereinafter identified, selected from a field of various carnation varieties maintained at my nursery for breeding purposes. This particular seedling was selected from those produced by the said crossing because of the unusual flower coloration on a plant having moderately abundant foliage, favorable growth characteristics and resistance to *Fusarium oxysporum*. After isolation of the selected plant, vegetative propagation was made by cuttings. The said propagation was made at our laboratory located in Le Pradet (France). Under my direction, propagation was done by means of cuttings. The initial success of the propagation continued through several successive generations which proved that the new variety retained all of the distinguished characteristics hold true from generation to generation and appear to be firmly fixed.

DESCRIPTION OF THE DRAWINGS

My new spray carnation cultivar is illustrated by the accompanying photographic drawing which, in full color, shows the form and coloration of the flowers as they appear. The colors shown are as nearly true to these herein specified as is reasonably possible to obtain by conventional photographic procedures.

DESCRIPTION OF THE NEW PLANT

The following is a detailed description of my new carnation plant as observed from plants grown under greenhouse conditions in Le Pradet, France with the stated flower colors being according to The R.H.S. Colour Chart of The Royal Horticultural Society of London, England.

THE PLANT

Origin:
Parentage:
*Seed parent.*—Plant number 83MP8.
*Pollen parent.*—Plant number 82MG7. These parent plants are so identified in my business records of the present cultivar maintained at the office of the Le Pradet, France nursery and the production of the aforementioned hybrid and the selected seedling are also there recorded.

Classification:
*Botanic.*—*Dianthus caryophyllus* L.
*Commercial.*—Spray carnation.
Form: An erect bush having at least 4 stems emitted near the ground having vigorous upright growth habit.
Height: About 75 cm (at 8 months)
Cane length: Less than 15 cm.
Branching character: Moderately branched.
Strength: Moderately rigid.
Foliage:
*Quantity.*—Moderately abundant.
*Number of leaves.*—More than 120.
*Size and shape of leaf.*—The leaf is 11.5×0.8 cm. at the 7th node and is spindle-shaped.
*Margin type.*—Straight.
*Texture.*—Leathery.
*Color.*—Upper side — RHS 137B. Under side — RHS 137B.

THE BUD

Size:
*Shape.*—Ovoid.
*Diameter.*—1.4 cm.
*Length.*—2.6 cm.
*Color of petals.*—When sepals first divide — RHS 39-D; When sepals begin to unfurl — RHS 39D.
Rate of opening: Normal.
Sepals:
*Shape.*—Joined at the lower part and sharp-pointed at extremity, "hooded" over bud.
*Number.*—5 to 6.
*Color.*—Inside: Pea green RHS 149D and 137D. Outside: Green RHS 137C and 144C
*Striae.*—Longitudinal striae.
Calyx:
*Shape.*—Cylindrical.
*Size.*—Long.
*Aspect.*—Smooth.
*Splitting.*—No. Color: RHS144C.
Peduncle:
*Length.*—About 57 cm.
*Character.*—Erect, rigid.
*Color.*—RHS 137B.

THE FLOWER

Blooming habit: Recurrent and profuse.
Size of bloom: Medium.

*Diameter.*—About 5.8 cm.
*Depth.*—About 4.7 cm.
Borne: Cluster.
Shape: High center when bloom first opens, dome when bloom matures.
*Number of blooms per cluster.*—An average of 6 between March and May.
Petalage:
*Number of petals.*—36 to 44.
*Form.*—Fan-shaped.
*Texture.*—Leathery.
*Appearance.*—Satiny.
*Color.*—Outer petals: Jasper red and Azalea pink body (39C and 39D) with a greenish base; Reverse side — Azalea pink and Orient pink (39D and 36D). Inside petals: Jasper red and Azalea pink body (39C and 39D) with a greenish base; Reverse side — Azalea pink and Orient pink (39D and 36D).
Petaloids:
*Number.*—1 to 5.
*Size.*—Smaller than petal.
*Color.*—Same as petal.
Discoloration after full bloom: Discoloration after full bloom may reach the color RHS 36-D.
Persistence: Yes.
Lasting quality: As cut flower, at least 10 days.
Disease resistance: *Fusarium oxysporum.*
Fragrance: Perceptible.

REPRODUCTIVE ORGANS

Stamens:
*Number.*—6 to 8.
*Arrangement.*—Around the ovary.
Anthers:
*Size.*—Less than 0.4 cm.
*Color.*—Whitish.
Filaments:
*Length.*—About 1.2 cm.
*Color.*—Whitish.
Pistils:
*Number.*—2 to 3.
Styles:
*Length.*—About 1.9 cm.
*Color.*—Whitish.
Stigmas: Whitish.
Character of ovaries: Ribbed.
*Color.*—Greenish.

I claim:

1. A new and distinctive hybrid spray carnation plant, substantially as herein shown and described, characterized in particular by its recurrent profuse production of medium sized flowers, the round petals of which are in general of Jasper red and Azalea pink color with a reverse side of Azalea pink and Orient pink color, said plant having more than 120 leaves on thick stems with moderately abundant foliage.

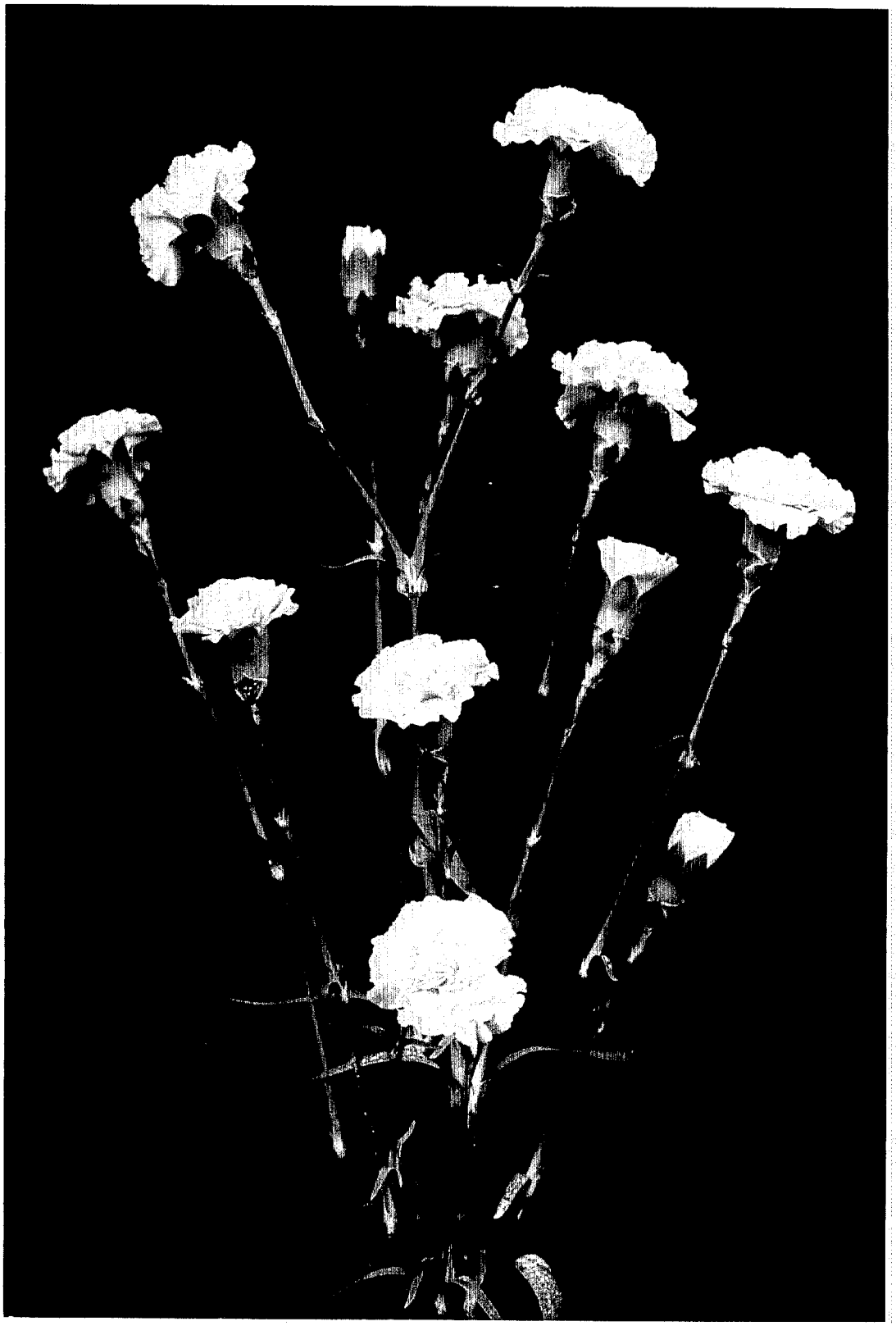

* * * * *